United States Patent [19]

Rody et al.

[11] Patent Number: 4,481,315

[45] Date of Patent: Nov. 6, 1984

[54] POLYALKYLPIPERIDINE LIGHT STABILIZERS

[75] Inventors: Jean Rody, Riehen; Mario Slongo, Muttenz, both of Switzerland

[73] Assignee: Ciba-Geigy Corporation, Ardsley, N.Y.

[21] Appl. No.: 470,742

[22] Filed: Feb. 28, 1983

Related U.S. Application Data

[60] Continuation of Ser. No. 266,873, May 26, 1981, abandoned, which is a division of Ser. No. 76,106, Sep. 17, 1979, Pat. No. 4,289,686.

[30] Foreign Application Priority Data

Sep. 27, 1978 [CH] Switzerland ............................ 7810088

[51] Int. Cl.$^3$ ............................................... C08K 5/34
[52] U.S. Cl. ........................................ 524/89; 524/91; 524/99; 524/100; 524/101; 524/102; 524/103; 542/435; 542/476; 544/198; 544/209; 544/212; 544/219; 546/19; 546/20; 546/187; 546/189; 546/190; 546/199; 546/221; 546/222; 546/223; 546/224; 546/225; 546/226; 546/227; 546/234; 546/235; 546/237; 546/239

[58] Field of Search ........................ 524/87, 91, 92, 93, 524/99, 100, 101; 542/435, 476; 544/198, 209, 212, 219; 546/19, 20, 187, 189, 190, 199, 221, 222, 223, 224, 225, 226, 227, 234

[56] References Cited

U.S. PATENT DOCUMENTS

| | | | |
|---|---|---|---|
| 4,085,089 | 4/1978 | Irick et al. | 524/91 |
| 4,118,369 | 10/1978 | Minagawa et al. | 524/101 |
| 4,127,501 | 11/1978 | Wang et al. | 252/403 |
| 4,161,592 | 7/1979 | Evans | 544/198 |
| 4,182,703 | 1/1980 | Irick et al. | 524/97 |
| 4,191,683 | 3/1970 | Brunetti et al. | 524/102 |

*Primary Examiner*—Richard A. Schwartz
*Attorney, Agent, or Firm*—Harry Falber

[57] ABSTRACT

Compounds which contain, in their molecule, at least one 2-(2'-hydroxyphenyl)-benztriazole group or one 2-hydroxybenzophenone group and at least one polyalkylpiperidine group are effective light stabilizers for organic materials, in particular for polymers. The use of the compounds as light stabilizers for lacquers is of particular importance.

12 Claims, No Drawings

POLYALKYLPIPERIDINE LIGHT STABILIZERS

This is a continuation of application Ser. No. 266,873 filed on May 26, 1981, now abandoned, which in turn is a divisional of application Ser. No. 076,106, filed Sep. 17, 1979, now U.S. Pat. No. 4,289,686.

The invention relates to novel light stabilisers for organic materials which are damaged by UV light, and in particular for organic polymers. These light stabilisers are molecular combinations of benztriazoles or 2-hydroxybenzophenones and polyalkylpiperidine derivatives.

It is known that 2-(2'-hydroxyphenyl)-benztriazoles and 2-hydroxybenzophenones are valuable light stabilisers for organic materials. They act as UV absorbers, i.e. they convert light quanta of high energy (UV light) into heat, which has no adverse effect on the organic material to be protected.

It is further known that polyalkylpiperidines are also valuable light stabilisers, which, however, do not act as UV absorbers since they do not absorb in shortwave light. It has hitherto not been possible clearly to clarify the mechanism of the action, cf, for example, H. J. Heller and H. R. Blattmann, Pure and Applied Chemistry, 36 (1973), 141–161.

Surprisingly, it has been found that molecular combinations of benztriazoles or hydroxybenzophenones on the one hand and polyalkylpiperidines on the other hand possess a light stabilising action which is far greater than can be expected from the sum of the two components. Such synergism was not foreseeable.

The invention therefore relates to compounds which contain, in their molecule, both at least one 2-(2'-hydroxyphenyl)-benztriaozole group or one 2-hydroxybenzophenone group and also at least one polyalkylpiperidine group, especially compounds which contain one or two groups of the formula AI or AII

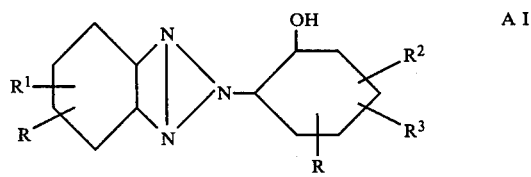

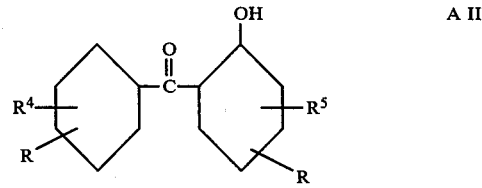

and one or two of the groups B I to B XII

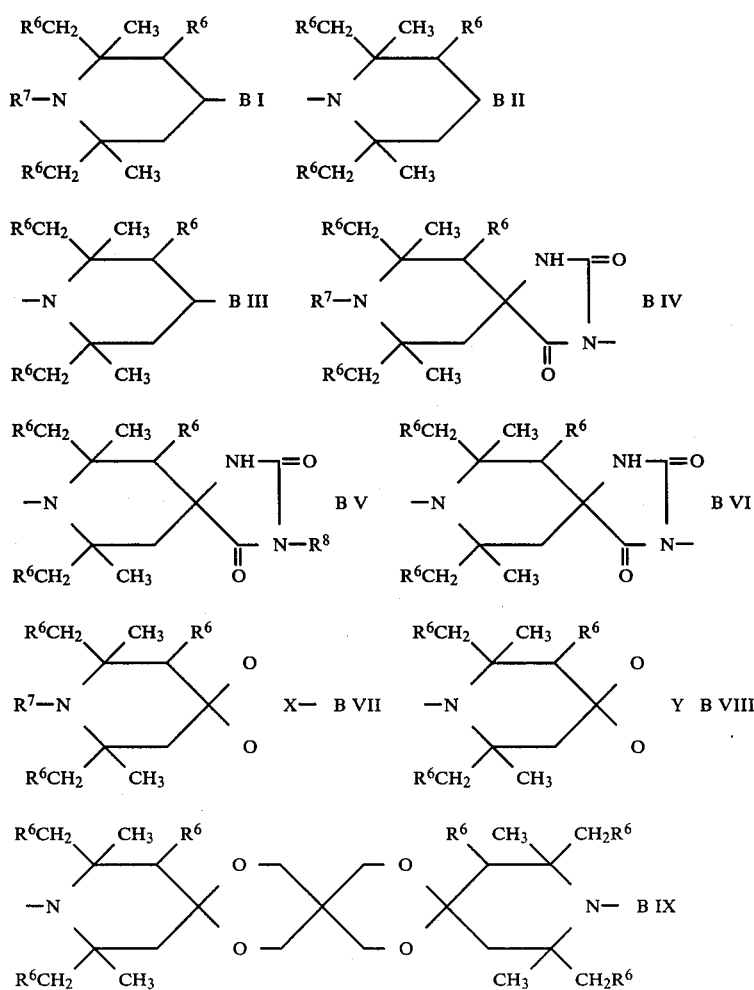

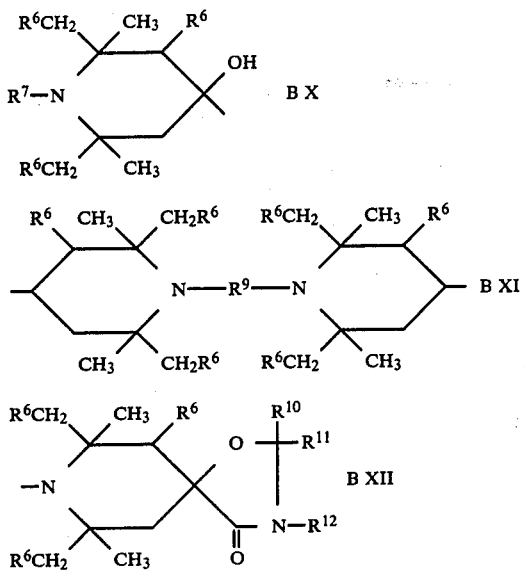

in which R is hydrogen or a free valency, $R^1$ is hydrogen, chlorine, $C_1$–$C_4$ alkyl, OH or $C_1$–$C_4$ alkoxy, $R^2$ and $R^3$ independently of one another are H, Cl, $C_1$–$C_{12}$ alkyl, $C_5$–$C_8$ cycloalkyl, phenyl, $C_7$–$C_9$ phenylaklyl, OH or $C_1$–$C_{12}$ alkoxy, $R^4$ and $R^5$ indepenently of one another are H, Cl, OH, $C_1$–$C_{12}$ alkyl, or $C_1$–$C_{12}$ alkyl, $R^6$ is H or $CH_3$, $R^7$ is H, O, $C_1$–$C_{12}$ alkyl, $C_3$–$C_8$ alkenyl, benzyl, acetyl or a group $-CH_2-CH(OH)-R^{13}$, $R^8$ is $C_1$–$C_{12}$ alkyl, $C_3$–$C_8$ alkenyl or $C_7$–$C_9$ phenylalkyl, $R^9$ is a $-CH_2CH=CHCH_2-$,

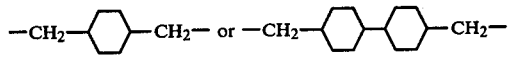

group, $R^{10}$ and $R^{11}$ are hydrogen, $C_1$–$C_{12}$ alkyl, phenyl or benzyl, or $R^{10}$ and $R^{11}$ are together $C_4$–$C_{19}$ alkylene, $R^{12}$ is H or a free valency, $R^{13}$ is H, $CH_3$, $C_2H_5$ or phenyl, X is a

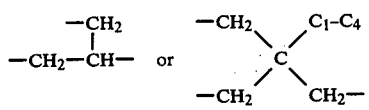

group and Y is a $C_2$–$C_8$ alkylene group, the groups A being linked to the groups B by a direct bond or by a divalent linking member —Z— and it being possible for —Z— to be one of the following groups: $-(CH_2)_m-CO-O-$, $-(CH_2)_m-CO-O-R^{14}-$, $-O-(CH_2)_n-CO-O-R^{14}-$, $-CH_2-CH(OH)-CH_2-O-CO-(CH_2)_m-$, $-O-CH_2-CH(OH)-CH_2-O-CO-(CH_2)_m-$, $-CH_2-CH(OH)-CH_2-$, $-CH_2-CH(OH)-CH_2-O-$, $-CH_2CH(OH)-CH_2-N(R^{15})-(CH_2)_m-$, $-O-CH_2-CH(OH)-CH_2-N(R^{15})-(CH_2)_m-$, $-N(R^{15})-CH_2-CH(OH)-CH_2-N(R^{16})-(CH_2)_m-$, $-CH_2-CH(R^{13})-O-CH_2-CH(OH)-CH_2-N(R^{15})-(CH_2)_m-$, $-CH_2-CH(R^{13})-O-CH_2-CH(OH)-CH_2O-CO-(CH_2)_m-$, $-(CH_2)_m-N(R^{15})-CO-$, $-(CH_2)_m-N(R^{15})-CO-(CH_2)_n-$, $-O-(CH_2)_3-N(R^{15})-CO-(CH_2)_m-$, $-CH_2-NH-CO-CH_2-O-$, $-CH_2-O-CH(R^{13})-CH_2-$, $-CH_2-NH-CO-CH_2-N(R^{15})-(CH_2)_m-$, $-CH_2-NH-CO-CH_2CH_2-N(R^{15})-(CH_2)_m-$ or

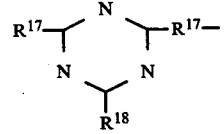

in which m is 0, 1 or 2, n is 1 or 2, $R^{14}$ is $-CH_2-$ or $-CH(R^{13})-CH_2-$, $R^{15}$ and $R^{16}$ are H, $C_1$–$C_{12}$-alkyl, cyclohexyl or benzyl, $R^{17}$ is $-O-$ or $-NR^{15}-$ and $R^{18}$ is $C_1$–$C_{12}$-alkoxy, phenoxy or an amino group

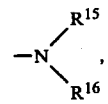

or the groups A and B being linked by a trivalent radical of the formula

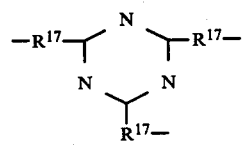

or a group AII being linked to a group B via a radical $-O-(CH_2)_n-CO-O-$.

If the groups A are linked to the groups B via divalent linking members Z, the following structures are possible: A—Z—B, B—Z—A—Z—B and A—Z—B—Z—A.

Analogous structures are possible if A and B are linked by direct bonds. If A and B are linked via a trivalent triazine radical T, the following structures are possible:

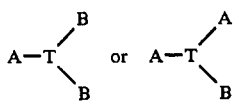

Alkyl $R^1$ can be, for example, methyl, ethyl, isopropyl or tert.-butyl. Alkyl $R^2$, $R^3$, $R^4$, $R^7$, $R^8$, $R^{10}$, $R^{11}$, $R^{15}$ and $R^{16}$ can in addition also be, for example, n-hexyl, 2-ethylhexyl, isononyl, n-decyl or n-dodecyl.

Cycloalkyl $R^2$ and $R^3$ can be, for example, cyclopentyl, cyclohexyl, dimethylcyclohexyl or cyclooctyl.

$C_3$-$C_8$ Alkenyl $R^7$ and $R^8$ can be, for example, allyl, methallyl, 2-hexenyl or 2-octenyl.

$C_7$-$C_9$ Phenylalkyl $R^2$, $R^3$ and $R^8$ can be, for example, benzyl, phenylethyl or phenylpropyl.

$C_1$-$C_4$ Alkoxy $R^1$ can be, for example, methoxy, ethoxy, isopropoxy or tert.-butoxy. $C_1$-$C_{12}$ Alkoxy $R^2$, $R^3$, $R^4$, $R^5$ and $R^{18}$ can in addition also be, for example, hexyloxy, octyloxy, nonyloxy or dodecyloxy.

$C_2$-$C_8$ Alkylene Y can be, for example, 1,2-ethylene, 1,2-propylene, 1,3-propylene, 1,2-butylene, 2,3-butylene, 2,2-dimethyl-1,3-propylene, 2-ethyl-1,3-propylene or 1,2-octylene. In the groups of the formula B VIII, Y together with the two oxygen atoms and the tertiary C atom forms a 5-membered or 6-membered ring.

If $R^{10}$ and $R^{11}$ together are $C_4$-$C_{19}$-alkylene, they form, together with the tertiary C atom to which they are bonded, a $C_5$-$C_{20}$-cycloalkane ring, for example a cyclopentane, cyclohexane, methylcyclohexane, cyclooctane, cyclododecane or cycloeicosane ring.

Preferably, $R^1$ is hydrogen or chlorine. Preferred B groups are the groups B I to B VI and amongst these those groups in which $R^6$ is hydrogen, $R^7$ is hydrogen, $C_1$-$C_8$ alkyl, allyl or benzyl and $R^8$ is $C_1$-$C_{12}$ alkyl, $C_3$-$C_5$ alkenyl or benzyl.

Preferred linking members Z are the groups —(CH$_2$)$_m$—CO—O—, —(CH$_2$)$_m$—CO—O—$R^{14}$, —O—(CH$_2$)$_n$—CO—O—, —O—(CH$_2$)$_n$—CO—O—$R^{14}$—, —(CH$_2$)$_m$—N($R^{15}$)—CO—, —(CH$_2$)$_m$—N($R^{15}$)—CO—(CH$_2$)$_n$—, —CH$_2$—NH—CO—CH$_2$—O— and —CH$_2$—NH—CO—CH$_2$—N($R^{15}$)—(CH$_2$)$_m$—.

Preferred triazine linking members are those in which $R^{17}$ is a group —N$R^{15}$—.

Examples of compounds according to the invention are the compounds of the following formulae:

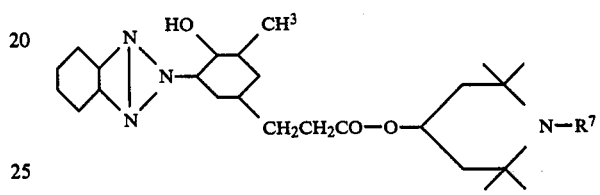

($R^7$ = H, CH$_3$, benzyl or acetyl)

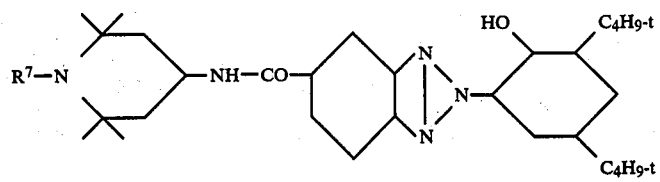

($R^7$ = H, O·, butyl or allyl)

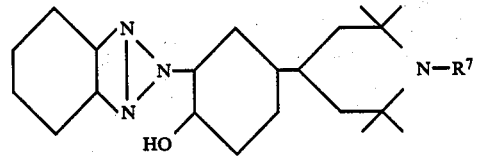

($R^7$ = H or CH$_3$)

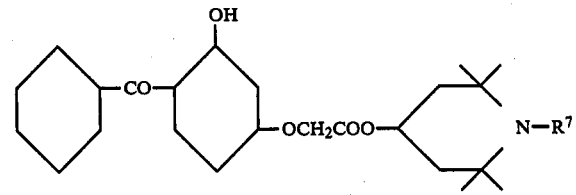

($R^7$ = H or CH$_3$)

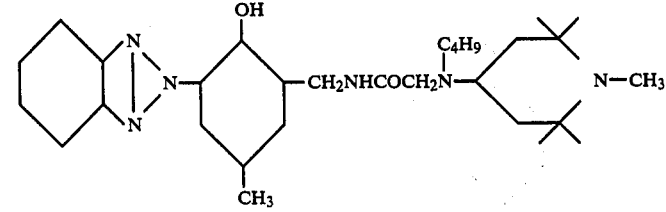

-continued
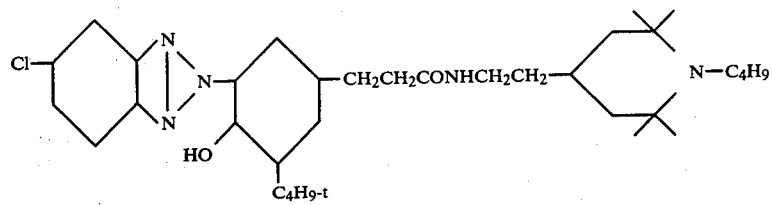
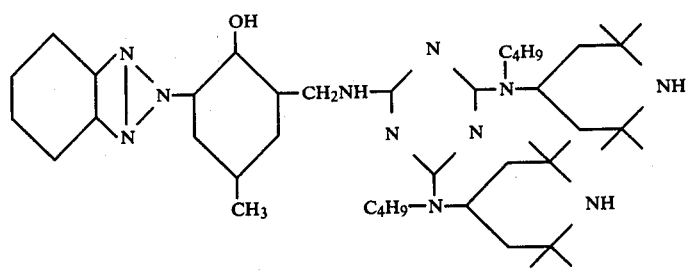
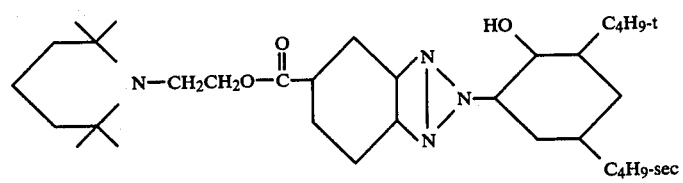
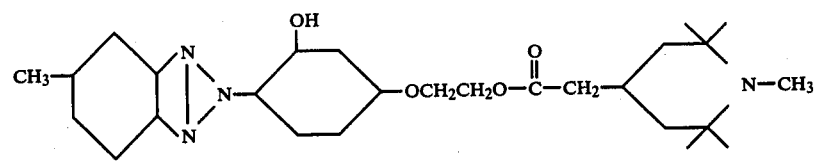
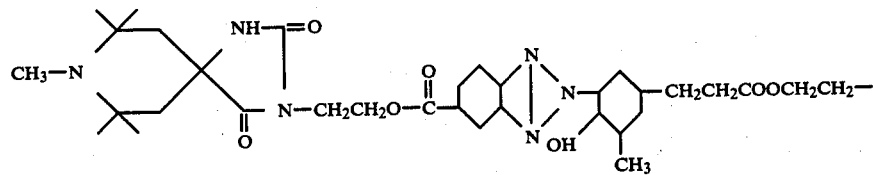
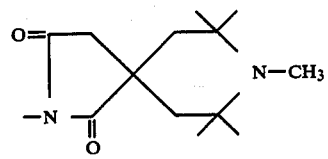
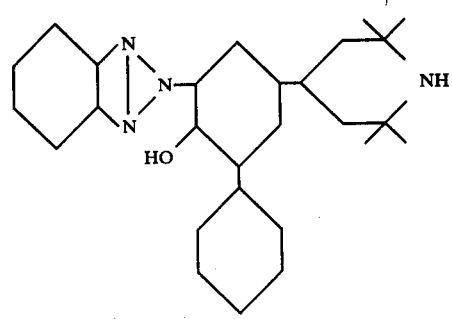

-continued
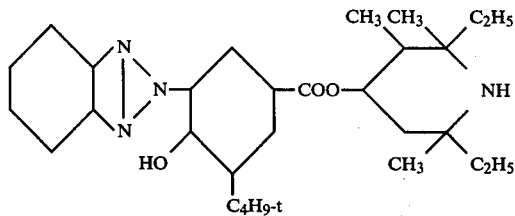
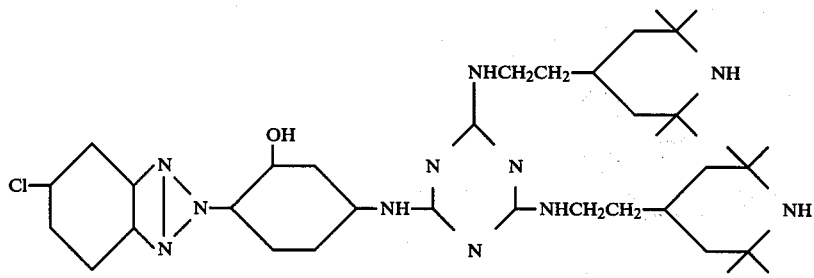
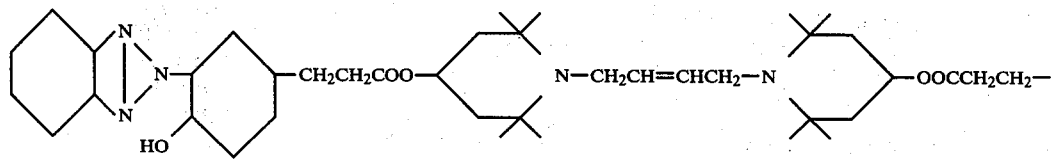
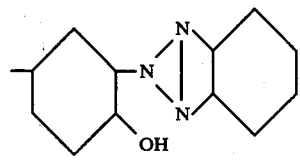
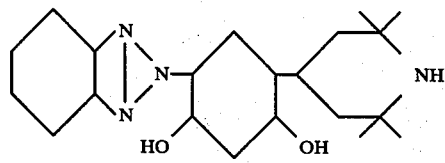
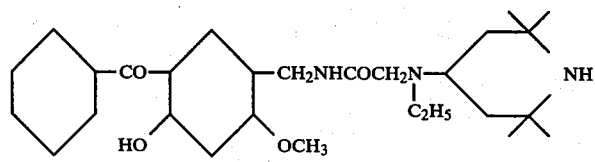
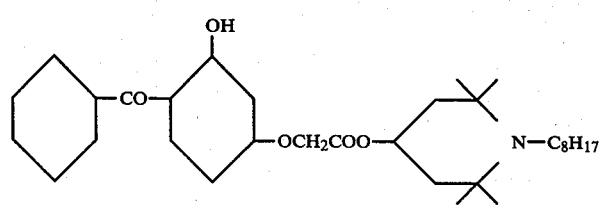
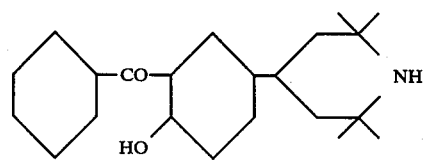

-continued

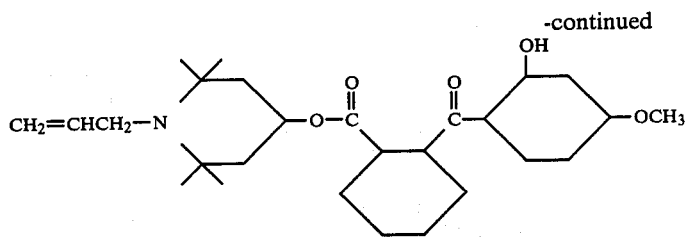

and

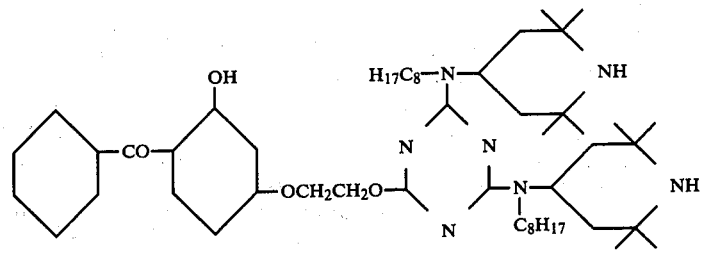

The starting material used to prepare the compounds according to the invention is a compound of the formula A I or A II, in which at least one R is a functional group which can react with a functional polyalkylpiperidine derivative.

If the group R is, for example, a carboxylic acid group —COOH, —CH$_2$CH$_2$COOH or —OCH$_2$COOH or a lower alkyl ester or acid chloride thereof, such a compound A I or A II can be reacted with a polyalkylpiperidine compound which carries a functional hydroxyl or amino group, for example, —OH, —CH$_2$C-H$_2$OH, —NH$_2$, —CH$_2$NH$_2$ or —CH$_2$CH$_2$NH$_2$.

If the group R is an amino group, for example —NH$_2$, —CH$_2$NH$_2$ or —CH$_2$CH$_2$NH$_2$, such a compound A I or A II can be reacted with a polyalkylpiperidine compound which carries a carboxyl group or a derivative thereof, for example an alkoxycarbonyl or chlorocarbonyl group. In both cases esters or amides are formed and the reaction is carried out by the customary methods for esterification or amidation.

If one of the two components carries an epoxyalkyl group and the other component carries an OH or NH group, linking members with ether or amine groups are formed.

Such compounds, in which the linking member is a triazine radical, are prepared by stepwise reaction of a dichlorotriazine or of cyanuric acid chloride with (a) an OH or NH derivative of AI or AII and (b) an OH or NH derivative of a polyalkylpiperidine.

In the case of the reaction of cyanuric acid chloride, this can be reacted either with 2 equivalents of the A derivative and 1 equivalent of the B derivative or 1 equivalent of the A derivative and 2 equivalents of the B derivative. However, it is also possible to react cyanuric acid chloride with 1 equivalent of an A derivative and 1 equivalent of a B derivative and the remaining chlorine is reacted with an amine, alcohol or phenol.

The functional derivatives of type A and type B which are required for this reaction are known compounds.

Thus, for example, carboxyl derivatives of A I are described in U.S. Pat. No. 3,766,205 and amino derivatives of A I are described in U.S. Pat. No. 3,159,646. Carboxyl or amino derivatives of A II are described in U.S. Pat. Nos. 2,983,708, 3,208,865 or 3,380,961.

Hydroxyl derivatives of polyalkylpiperidines are described, for example, in German Offenlegungsschriften Nos. 2,352,658, 2,353,538 and 2,402,636 and corresponding amino derivatives are described, for example, in German Offenlegungsschriften Nos. 2,040,975 and 2,352,379. Carboxyl derivatives of type B are described, for example, in German Offenlegungsschriften Nos. 2,337,865 and 2,719,133.

Compounds in which the group A is linked to group B by a direct bond are prepared by special methods. Thus, for example, coupling of 4-(4'-hydroxyphenyl)-2,2,6,6-tetramethylpiperidine with an o-nitrophenyldiazonium compound yields the corresponding o-nitroazo compound, which can be converted to the corresponding benztriazole by known reduction methods. The hydroxyphenylpiperidines required for this process are described in German Offenlegungsschrift No. 2,258,086.

Further details relating to the preparation of the compounds according to the invention are given in the examples which follow further below.

The novel compounds are outstanding light stabilisers for organic materials which are sensitive to the action of light, and especially for organic polymers. In particular, the compounds are distinguished by a powerful protective action against short-wave light (UV light).

The following are examples of polymers which can be stabilised by the addition of the compounds according to the invention:

1. Polymers of mono- and di-olefins, for example polyethylene (which can be crosslinked), polypropylene, polyisobutylene, polymethylbut-1-ene, polymethylpent-1-ene, polyisoprene or polybutadiene.

2. Mixtures of the polymers mentioned under (1), for example mixtures of polypropylene with polyethylene or with polyisobutylene, or, for example, mixtures of two polyethylenes of different density or of different melt index.

3. Copolymers of mono- and di-olefins, for example ethylene/propylene copolymers, propylene/but-1-ene copolymers, propylene/isobutylene copolymers and ethylene/but-1-ene copolymers and also terpolymers of ethylene with propylene and a diene, such as hexadiene, dicyclopentadiene or ethylidenenorbornene.

4. Polystyrene.

5. Copolymers of styrene or α-methylstyrene with dienes or acrylic derivatives, for example styrene/butadiene, styrene/acrylonitrile or styrene/acrylonitrile/methyl acrylate; mixtures of high impact strength obtained from styrene copolymers and another polymer, for example a polyacrylate, a diene polymer or an ethylene/propylene/diene terpolymer; and also block copolymers of styrene, for example styrene/butadiene/styrene, styrene/isoprene/styrene or styrene/ethylene-butylene/styrene.

6. Graft copolymers of styrene, for example styrene on polybutadiene, styrene and acrylonitrile on polybutadiene and mixtures thereof with the copolymers listed under (5), such as those known as ABS polymers.

7. Halogen-containing polymers, for example polyvinyl chloride, polyvinylidene chloride, polyvinyl fluoride, polychloroprene, chlorinated rubbers and copolymers such as vinyl chloride/vinylidene chloride, vinyl chloride/vinyl acetate or vinylidene chloride/vinyl acetate.

8. Polymers which are derived from α,β-unsaturated acids and their derivatives, such as polyacrylates and polymethacrylates, polyacrylamides and polyacrylonitrile.

9. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinyl butyrate, polyallyl phthalate, polyallylmelamine and their copolymers with other vinyl compounds, such as ethylene/vinyl acetate copolymers.

10. Homo- and co-polymers of epoxides, such as polyethylene oxide, polypropylene oxide or their copolymers with bis-glycidyl ethers.

11. Polyacetals, such as polyoxymethylene, and also those polyoxymethylenes which contain ethylene oxide as the comonomer.

12. Polyphenylene oxides.

13. Polyurethanes and polyureas.

14. Polycarbonates.

15. Polysulphones.

16. Polyamides and copolyamides which are derived from diamines and dicarboxylic acids and/or from aminocarboxylic acids or the corresponding lactams, such as polyamide 6, polyamide 6/6, polyamide 6/10, polyamide 11 and polyamide 12.

17. Polyesters which are derived from dicarboxylic acids and dialcohols and/or from hydroxycarboxylic acids or the corresponding lactones, such as polyethylene terephthalate, polybutylene terephthalate and poly-1,4-dimethylolcyclohexane terephthalate, and copolyetheresters.

18. Crosslinked polymers which are derived from aldehydes on the one hand and from phenols, ureas and melamines on the other hand, such as phenol-formaldehyde resins, urea-formaldehyde resins and melamine-formaldehyde resins.

19. Alkyd resins, such as glycerol/phthalic acid resins and their mixtures with melamine-formaldehyde resins.

20. Unsaturated polyester resins which are derived from copolyesters of saturated and unsaturated dicarboxylic acids with polyhydric alcohols and vinyl compounds as crosslinking agents, and also their halogen-containing modifications of low combustibility.

21. Crosslinked epoxide resins which are derived from polyepoxides, for example from bis-glycidyl ethers or from cycloaliphatic diepoxides.

22. Naturally occurring polymers, such as cellulose, rubber and proteins, and also their polymer-homologously chemically modified derivatives, such as cellulose acetates, cellulose propionates and cellulose butyrates and the cellulose ethers, such as methylcellulose.

Amongst these polymers, those of particular interest are those which can be used as binders for lacquers, especially for stoving lacquers, for example those of groups 18, 19, 20 and 21 in the above list. It has been found that in lacquers a combination of piperidine light stabilisers with UV absorbers is very valuable. In the case of stoving lacquers, the volatility of the customary low-molecular light stabilisers based on benztriazoles, benzophenones and polyalkylpiperidines presents a serious technical problem. By means of the chemical combination of the different types of light stabilisers according to the present invention, the volatility is greatly reduced, so that the novel compounds are also suitable for stabilising stoving lacquers.

The compounds according to the invention are added to the polymers in an amount of 0.05 to 5% by weight and preferably of 0.1 to 1% by weight.

The light stabilisers according to the invention are added to the polymer, before the latter is shaped, by mixing with the pulverulent polymer or with the melt or solution of the polymer or its precursors. At the same time, other additives such as are known and customary in plastics technology can also be incorporated in the polymer. These additives can be, for example, anti-oxidants, metal deactivators, other stabilisers, plasticisers, lubricants, blowing agents, pigments, fillers or other assistants. Individual examples of such known and customary additives for plastics are listed on pages 25–32 of German Offenlegungsschrift No. 2,349,962.

The polymers stabilised in this way can be used in very diverse forms, for example as films, fibres, tapes or profiles or as binders for lacquers, adhesives or putties.

The preparation and use of the compounds according to the invention are described in the examples which follow. In the examples parts and percentages are by weight. The temperatures are in °C.

EXAMPLE 1

46.7 g of 2-(2-hydroxy-3-methyl-5-β-methoxycarbonylethyl-phenyl)-benztriazole (prepared according to U.S. Pat. No. 3,766,205) are heated with 23.6 g of 2,2,6,6-tetramethyl-4-hydroxy-piperidine and 9 g of sodium methylate in 300 ml of xylene for 20 hours at 130°–135° under a gentle stream of nitrogen. The methanol formed is distilled off continuously. The reaction mixture is cooled to room temperature, acidified with acetic acid and extracted three times with, in each case, 100 ml of water. The combined aqueous extracts are rendered alkaline with ammonia and the resulting precipitate is filtered off, washed with water, dried and crystallised from ligroin. This yields 2-{2-hydroxy-3-methyl-5-[β-(2,2,6,6-tetramethyl-4-piperidinyloxycarbonyl)-ethyl]-phenyl}-benztriazole (compound 1) in the form of a virtually colourless powder with a melting point of 131°.

If an equivalent amount of 1,2,2,6,6-pentamethyl-4-hydroxypiperidine or of 1-benzyl-2,2,6,6-tetramethyl-4-hydroxypiperidine is used in place of 2,2,6,6-tetramethyl-4-hydroxypiperidine and in other respects the procedure followed is as described above, this yields 2-{2-hydroxy-3-methyl-5-[β-(1,2,2,6,6-pentamethyl-4-piperidinyloxycarbonyl)-ethyl]-phenyl}-benztriazole (compound 2) with a melting point of 110°–111° or, respectively, 2-{2-hydroxy-3-methyl-5-[β-(1-benzyl-2,2,6,6-tetramethyl-4-piperidinyloxycarbonyl)-ethyl]-phenyl}-benztriazole (compound 3) with a melting point of 127°-128°.

EXAMPLE 2

23.1 g of 2-(2-hydroxy-3,5-di-tert.-butyl-phenyl)-benztriazole-5-carboxylic acid chloride are initially introduced into 300 ml of toluene at room temperature. A solution of 10.1 g of 2,2,6,6-tetramethyl-4-aminopiperidine in 100 ml of toluene is added dropwise to this solution in the course of about 30 minutes and the reaction mixture is then stirred for 15 hours at room temperature. The hydrochloride which has precipitated is filtered off and dissolved in 200 ml of ethanol and 200 ml of water. The solution is rendered alkaline with sodium carbonate and the resulting precipitate is filtered off, washed with water, dried and crystallised from toluene. This yields 2-(2-hydroxy-3,5-di-tert.-butylphenyl)-benztriazole-5-carboxylic acid N-(2,2,6,6-tetramethyl-4-piperidinyl)-amide (compound 4) with a melting point of 267°.

If an equivalent amount of 2,2,6,6-tetramethyl-4-β-aminoethyl-piperidine is used in place of 2,2,6,6-tetramethyl-4-aminopiperidine and in other respects the procedure followed is as described above, this yields 2-(2-hydroxy-3,5-di-tert.-butyl-phenyl)-benztriazole-5-carboxylic acid N-[β-(2,2,6,6-tetramethyl-4-piperidinyl)-ethyl]-amide (compound 5) with a melting point of 228°.

EXAMPLE 3

57.2 g of 2-hydroxy-4-methoxycarbonyl-methoxy-benzophenone are heated with 36 g of 1,2,2,6,6-pentamethyl-4-hydroxypiperidine and 15 g of sodium methylate in 250 ml of xylene for 8 hours at 130°-135° under a gentle stream of nitrogen. The methanol formed is distilled off continuously during the trans-esterification. After cooling to room temperature, the reaction mixture is acidified with acetic acid and is then extracted three times with, in each case, 100 ml of water. The combined aqueous extracts are rendered alkaline with ammonia and the precipitate is filtered off, washed with water, dried and recrystallised from ethylene glycol monomethyl ether. This yields 2-hydroxy-4-(1,2,2,6,6-pentamethyl-4-piperidinyloxycarbonyl-methoxy)-benzophenone (compound 6) with a melting point of 79°.

EXAMPLE 4

12.5 g of o-nitroaniline are diazotised by known processes and the resulting diazonium salt solution is added dropwise to a solution of 16.3 g of 2,2,6,6-tetramethyl-4-(4'-hydroxyphenyl)-piperidine in 100 ml of water and 4 g of sodium hydroxide, at 0°-5° and a pH of 10-12. After the coupling reaction has ended, the pH of the reaction mixture is adjusted to 7 with acetic acid and the azo dye is filtered off. After drying at 50° in vacuo, the azo dye (19.1 g) is dissolved in 50 ml of ethylene glycol monomethyl ether. A solution of 6 g of sodium hydroxide in 20 ml of water is added to this solution and the mixture is warmed to 80°. 2.5 g of hydrazine hydrate are added dropwise at this temperature in the course of about 15 minutes and the reaction mixture is then stirred for a further 1 hour at 80°. During this time the colour of the reaction mixture changes from violet to brown. The mixture is cooled to room temperature and 6.5 g of zinc dust are added in portions in the course of about 30 minutes. The reaction mixture is then warmed to 60°, a further 6.5 g of zinc dust and 25 ml of 10 N sodium hydroxide solution are added and the resulting mixture is stirred for a further 1 hour. The pale green reaction mixture is filtered to remove the zinc sludge and about 70 ml of glacial acetic acid are slowly added to the filtrate (pH ~6) and the resulting solution is clarified and then rendered alkaline with ammonia. The resulting precipitate is filtered off, washed with water, dried and crystallised from ligroin. This yields 2-[2-hydroxy-5-(2,2,6,6-tetramethylpiperidin-4-yl)-phenyl]-benztriazole (compound 7) with a melting point of 178°-180°.

If an equivalent amount of 2,2,6,6-tetramethyl-4-(3'-methyl-4'-hydroxyphenyl)-piperidine or 2,2,6,6-tetramethyl-4-(3'-butyl-4'-hydroxyphenyl)-piperidine or 2,2,6,6-tetramethyl-4-(3'-cyclohexyl-4'-hydroxyphenyl)-piperidine or 2,2,6,6-tetramethyl-4-(2'-hydroxy-5'-methylphenyl)-piperidine is used in place of 2,2,6,6-tetramethyl-4-(4'-hydroxyphenyl)-piperidine and in other respects the procedure followed is as described above, this yields, respectively, 2-[2-hydroxy-3-methyl-5-(2,2,6,6-tetramethylpiperidin-4-yl)-phenyl]-benztriazole (compound 8) with a melting point of 219°-220°, or 2-[2-hydroxy-3-t-butyl-5-(2,2,6,6-tetramethylpiperidin-4-yl)-phenyl]-benztriazole (compound 9) with a melting point of 162°-64°, or 2-[2-hydroxy-3-cyclohexyl-5-(2,2,6,6-tetramethylpiperidin-4-yl)-phenyl]-benztriazole (compound 10) with a melting point of 155°-56°, or 2-[2-hydroxy-3-(2,2,6,6-tetramethylpiperidin-4-yl)-5-methyl-phenyl]-benztriazole (compound 11) with a melting point of 168°-69°.

EXAMPLE 5

20 g of 2-[2-hydroxy-3-methyl-5-(2,2,6,6-tetramethylpiperidin-4-yl)-phenyl]-benztriazole (compound 8) are dissolved in 150 ml of formic acid (98%). 87.4 ml of a 35% formaldehyde solution are then added dropwise in the course of about 1 hour, at room temperature. The light brownish solution is then heated under reflux for 20 hours, cooled to room temperature and added dropwise to a cold saturated potassium carbonate solution. The white crystalline precipitate is filtered off, washed with water, dried and recrystallised from ligroin. This yields 2-[2-hydroxy-3-methyl-5-(1,2,2,6,6-pentamethyl-piperidin-4-yl)-phenyl]-benztriazole with a melting point of 206°-207° (compound 12).

EXAMPLE 6

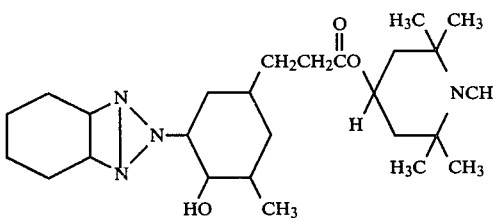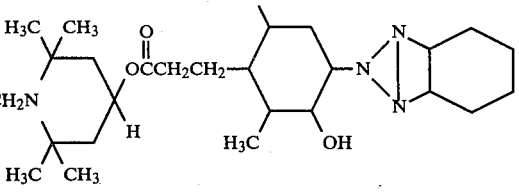

130.7 g of 2-(2-hydroxy-3-methyl-5-β-methoxycarbonyl-ethyl-phenyl)-benztriazole and 73.3 g of 1,4-bis-(2,2,6,6-tetramethyl-4-hydroxypiperidin-1-yl)-but-2-ene are heated in 600 ml of xylene for 24 hours at 130°–35° under a gentle stream of nitrogen, after adding 1.0 g of tetrabutyl orthotitanate. The methanol formed is distilled off continuously. After this time, 1.0 g of tetrabutyl orthotitanate is added and the transesterification is carried out for a further 24 hours at 130°–35°. The xylene is now extensively distilled off and the residue is recrystallised twice from ligroin. This yields the diester of the above structure (compound 13) as virtually colourless crystals with a melting point of 135°.

EXAMPLE 7

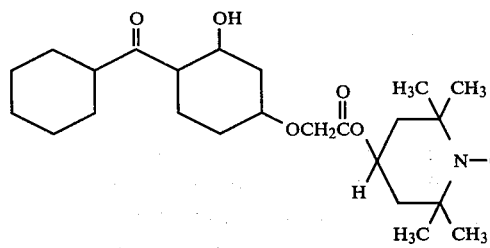

30.0 g of 2-hydroxy-4-methoxycarbonyl-methoxybenzophenone are heated with 10.0 g of 1-hydroxyethyl-2,2,6,6-tetramethyl-4-hydroxypiperidine and 0.5 g of tetrabutyl orthotitanate in 200 ml of xylene for 15 hours at 130°–35° under a gentle stream of nitrogen. The methanol formed is distilled off continuously during the trans-esterification. After the addition of a further 0.5 g portion of tetrabutyl orthotitanate, the transesterification is carried out for a further 15 hours. The reaction solution is clarified and evaporated and the residue is recrystallised from toluene/hexane. This yields the diester having the structure given above (compound 14) as yellowish crystals with a melting point of 130°.

EXAMPLE 8

Light stabilisation of a 2-coat metallic lacquer (1) Formulations (a) Base lacquer (pigmented)

| | |
|---|---|
| 54.4 g | of L 1850 polyester (Dynamit Nobel AG, Troisdorf, West Germany) |
| 5.5 g | of Maprenal MF 650 melamine resin (Cassella-Hoechst AG, Wiesbaden, West Germany) |
| 3.7 g | of toluene |
| 2.8 g | of n-butanol |
| 3.7 g | of butyl acetate |
| 20.7 g | of Alcoa 726 (Alcoa GmbH, Frankfurt/M, West Germany, a 40% dispersion of aluminium-bronze in 1:1 xylene/butyl acetate |
| 9.2 g | of EAB 551-0.01 cellulose acetobutyrate (Eastman Chem. Corp., Zug, Switzerland) |

-continued

| |
|---|
| 100 g |

Before application, the base lacquer was diluted with a 1:1 mixture of xylene/butyl acetate to a viscosity corresponding to a flow time of 15 seconds in a type 4 Ford cup.

(b) Clear lacquer (top coat)

| | |
|---|---|
| 100 g | of acrylic resin based on a hydroxyethyl acrylate copolymer |
| 30 g | of resin hardener (Desmodur N, Bayer A.G., Leverkusen, West Germany) |
| 3 g | of flow aid (Byketol Spezial, Byk-Mallinckrodt, Wesel, West Germany) |
| 53 g | of 30:30:40 solvent mixture of ethylglycol acetate/butyl acetate xylene |
| 186 g | |

The hardener was not admixed until shortly before application. The stabilisers mentioned in section 5 were also added at this stage.

(2) Preparation of the samples

56×67 mm aluminium plates were coated with a bonding adhesive (filling primer from Messrs. Dr. Herberts) and stoved for 15 minutes at 175°.

An approximately 15 μm thick coat of the pigment-containing base lacquer was then sprayed on and, after a short period of drying at room temperature, an approximately 35 μm thick coat of the clear lacquer was sprayed on. The 2-coat lacquer was stoved at 80° C., for 30 minutes and the sample was stored for 4 weeks in a normal climate (23° C./50% relative atmospheric humidity).

(3) Weathering (a) Accelerated weathering in a QUV weathering device from Messrs. Q-Panel Corp., U.S.A., in accordance with ASTM G 53-77. In this test, the samples were alternately weathered dry for 4 hours at 60° C. and moist for 4 hours at 50° C. Weathering was carried out for a total of 900 hours.

(b) Florida weathering. The samples were weathered for 12 months in the open in a black box inclined 5° to the south.

(4) Evaluation of the samples

The following were measured:

(a) The gloss-reflection at an angle of 20° in accordance with DIN 67 530 or ASTM D 523.

(b) The crazing in accordance with the TNO crazing assessment scale.

(c) The total colour shade difference ΔE in accordance with DIN 6174.

(d) The colour change by means of the grey scale in accordance with ISO-Recom. R 105/Part 2.

(5) Light stabilisers used

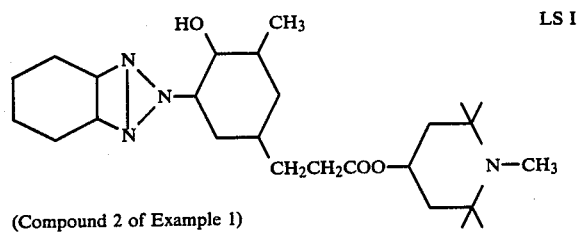

(Compound 2 of Example 1)

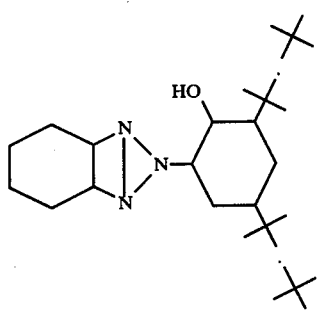

(Commercially available UV absorber)

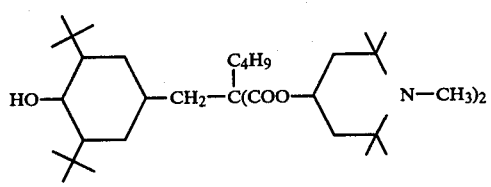

(Commercially available light stabiliser based on polyalkylpiperidine)

(6) Results (a) Accelerated weathering

| Light stabiliser* | Gloss reflection | | Colour shade difference ΔE | Crazing assessment** |
|---|---|---|---|---|
| | before weathering | after weathering | | |
| none | 95 | 84 | 9.4 | F 7c |
| 1% LS I | 96 | 96 | 4.5 | 0 |
| 2% LS I | 96 | 96 | 3.0 | 0 |
| 1% LS II + 1% LS III | 94 | 98 | 4.7 | F 4a |

(b) Florida weathering

| Light stabiliser* | Gloss/reflection | | Colour change (grey shade) | Crazing assessment** |
|---|---|---|---|---|
| | before weathering | after weathering | | |
| none | 95 | 21 | 3 | F 8 |
| 1% LS I | 96 | 83 | 4 | 0 |
| 2% LS I | 96 | 85 | 4 | 0 |
| 1% LS II + 1% LS III | 94 | 73 | 4 | 0 |

*The indicated amount of light stabiliser is calculated relative to the solids content (resin + hardener) of the clear lacquer.
**Crazing assessment 0 means: no visible crazing.

What is claimed is:

1. A compound of the formula A—B or A—Z—B wherein A is one of the groups

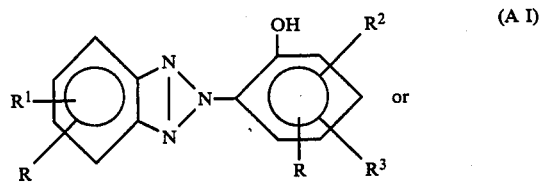

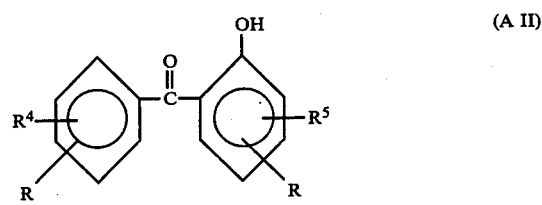

and B is one of the groups

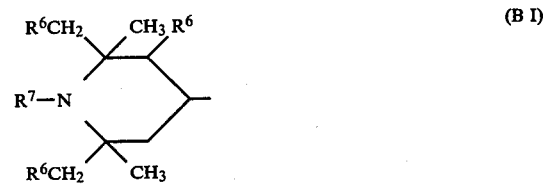

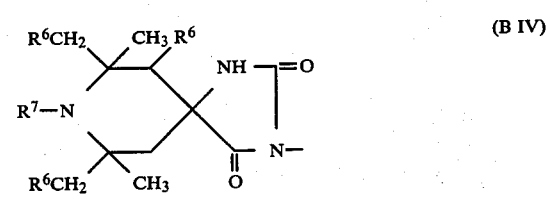

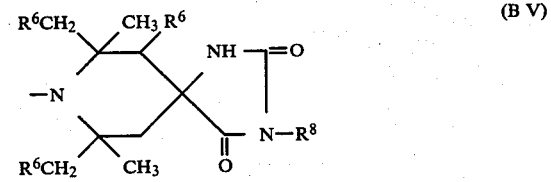

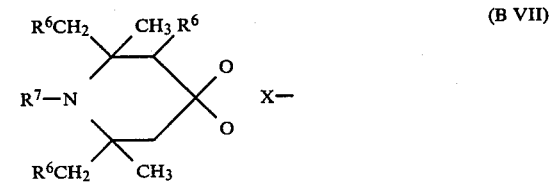

-continued

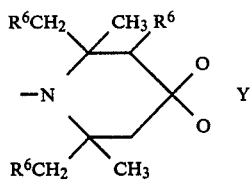
(B VIII)

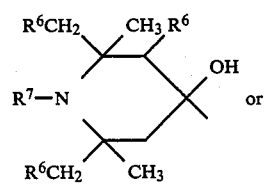
(B X)

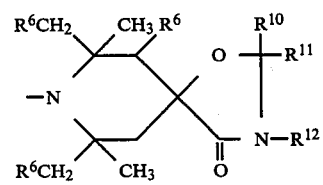
(B XII)

in which one R is H and the other R is a free valency; $R^1$ is H, Cl, $C_1-C_4$ alkyl, OH or $C_1-C_4$ alkoxy; $R^2$ and $R^3$ independently of one another are H, Cl, $C_1-C_{12}$ alkyl, $C_5-C_8$ cycloalkyl, phenyl, $C_7-C_9$ phenylalkly, OH or $C_1-C_{12}$ alkoxy; $R^4$ and $R^5$ independently of one another are H, Cl, OH, $C_1-C_{12}$ alkoxy or $C_1-C_{12}$ alkyl; $R^6$ is H or $CH_3$; $R^7$ is H, O, $C_1-C_{12}$ alkyl, $C_3-C_8$ alkenyl, benzyl, acetyl or a group —$CH_2$—$CH(OH)$—$R^{13}$; $R^8$ is $C_1-C_{12}$ alkyl, $C_3-C_8$ alkenyl or $C_7-C_9$ phenylalkyl; $R^{10}$ and $R^{11}$ are hydrogen, $C_1-C_{12}$ alkyl, phenyl or benzyl, or $R^{10}$ and $R^{11}$ are together $C_4-C_{19}$ alkylene; $R^{12}$ is H; $R^{13}$ is H, $CH_3$, $C_2H_5$ or phenyl; X is a

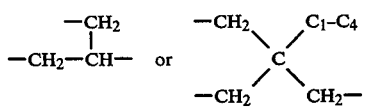

alkyl group; Y is $C_2-C_8$ alkylene; and —Z— is one of the following groups: —$(CH_2)$—CO—O—, —$(CH_2)_m$—CO—O—$R^{14}$—, —O—$(CH_2)_n$—CO—O—$R^{14}$—, —$CH_2$—$CH(OH)$—$CH_2$—O—CO—$(CH_2)_m$—, —O—$CH_2$—$CH(OH)$—$CH_2$—O—CO—$(CH_2)_m$—, —$CH_2$—$CH(OH)$—$CH_2$—, —$CH_2$—$CH(OH)$—$CH_2$—O—, —$CH_2$—$CH(OH)$—$CH_2$—$N(R^{15})$—$(CH_2)_m$—, —O—$CH_2$—$CH(OH)$—$CH_2$—$N(R^{15})$—$(CH_2)_m$—, —$N(R^{15})$—$CH_2$—$CH(OH)$—$CH_2$—$N(R^{16})$—$(CH_2)_m$—, —$CH_2$—$CH(R^{13})$—O—$CH_2$—$CH(OH)$—$CH_2$—$N(R^{15})$—$(CH_2)_m$—, —$CH_2$—$CH(R^{13})$—O—$CH_2$—$CH(OH)$—$CH_2$—O—CO—$(CH_2)_m$—, —$(CH_2)_m$—$N(R^{15})$—CO—, —$(CH_2)_m$—$N(R^{15})$—CO—$(CH_2)_n$—, —O—$(CH_2)_3$—$N(R^{15})$—CO—$(CH_2)_m$—, —$CH_2$—NH—CO—$CH_2$—O—, —$CH_2$—NH—CO—$CH_2$—O—$CH(R^{13})$—$CH_2$—, —$CH_2$—NH—CO—$CH_2$—$N(R^{15})$—$(CH_2)_m$—, —$CH_2$—NH—CO—$CH_2$—$CH_2$—$N(R^{15})$—$(CH_2)_m$— or

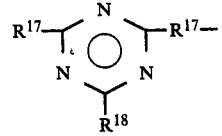
(B VIII)

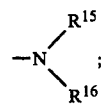

in which m is 0, 1 or 2, n is 1 or 2, $R^{14}$ is —$CH_2$— or —$CH(R^{13})$—$CH_2$—, $R^{15}$ and $R^{16}$ are H, $C_1-C_{12}$-alkyl, cyclohexyl or benzyl, $R^{17}$ is —O— or —$NR^{15}$— and $R^{18}$ is $C_1-C_{12}$-alkoxy, phenoxy or an amino group or a group AII is linked to a group B via a radical —O—$(CH_2)_n$—CO—O—.

2. A compound according to claim 1 which contains a group B I, B II, B IV or B V, in which $R^6$ is hydrogen, $R^7$ is hydrogen, $C_1-C_8$ alkyl, allyl or benzyl and $R^8$ is $C_1-C_{12}$ alkyl, $C_3-C_5$ alkenyl or benzyl.

3. A compound according to claim 1, which contains a group of the formula A I, in which $R^1$ is hydrogen or chlorine.

4. A compound according to claim 1, in which the groups A are linked to the groups B by a direct bond or one of the groups —$(CH_2)_m$—CO—O—, —$(CH_2)_m$—CO—O—$R^{14}$—, —O—$(CH_2)_n$—CO—O—$R^{14}$—, —$(CH_2)_m$—$N(R^{15})$—CO—, —$(CH_2)_m$—$N(R^{15})$—CO—$(CH_2)_n$—, —$CH_2$—NH—CO—$CH_2$—O— or —$CH_2$—NH—CO—$CH_2$—$N(R^{15})$—$(CH_2)_m$—.

5. The compound according to claim 1, of the formula

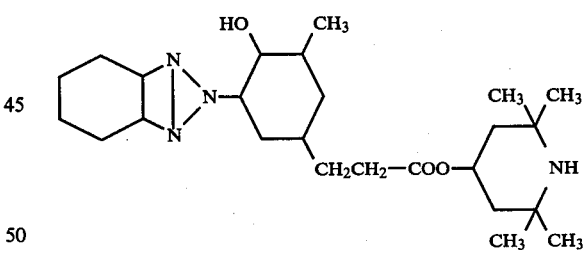

6. The compound according to claim 1, of the formula

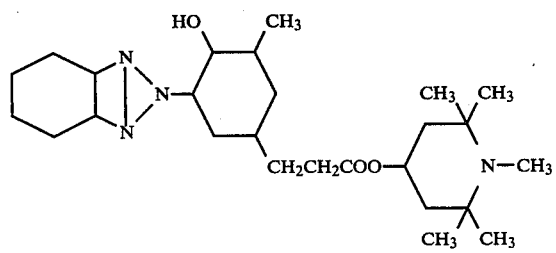

7. The compound according to claim 1, of the formula

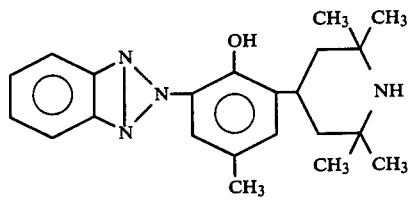

8. The compound according to claim 1, of the formula

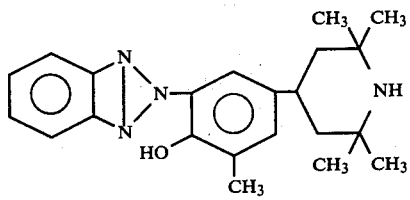

9. A method of stabilizing a polymer normally subject to deterioration by light which comprises incorporating into said polymer an effective stabilizing amount of a compound according to claim 1.

10. The method of claim 9, wherein said polymer is a binder for lacquers.

11. A composition of matter stabilized against light induced deterioration comprising a polymer normally subject to deterioration by light and 0.05 to 5%, by weight, of a compound of claim 1.

12. The composition of claim 11, wherein said polymer is a binder for lacquers.

* * * * *

UNITED STATES PATENT AND TRADEMARK OFFICE
CERTIFICATE OF CORRECTION

PATENT NO. : 4,481,315

DATED : November 6, 1984

INVENTOR(S) : Jean Rody and Mario Slongo

Page 1 of 4

It is certified that error appears in the above-identified patent and that said Letters Patent is hereby corrected as shown below:

Claim 1, Column 20, Lines 62-68 should read--

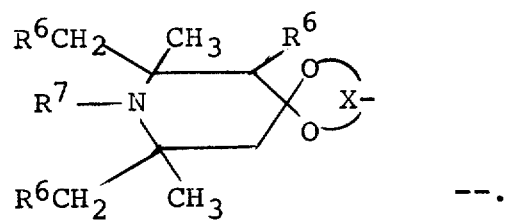

--.

Claim 1, Column 21, Lines 2-8 should read--

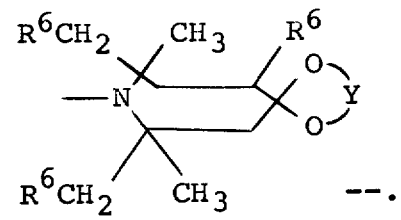

--.

UNITED STATES PATENT AND TRADEMARK OFFICE
CERTIFICATE OF CORRECTION

PATENT NO. : 4,481,315
DATED : November 6, 1984
INVENTOR(S) : Jean Rody and Mario Slongo It is certified that error appears in the above-identified patent and that said Letters Patent is hereby corrected as shown below:

Claim 1, Column 21, Lines 43-48 should read--

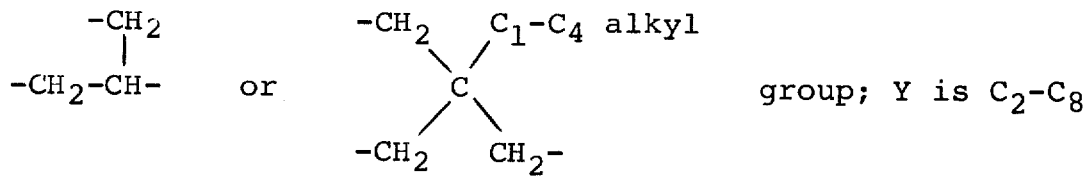

alkylene; and -Z- is one of --.

Claim 1, Column 21, Line 49 should read-- the following groups: $-(CH_2)_m-CO-O-, -(CH_2)_m$ --.

UNITED STATES PATENT AND TRADEMARK OFFICE
CERTIFICATE OF CORRECTION

PATENT NO. : 4,481,315

DATED : November 6, 1984

INVENTOR(S) : Jean Rody and Mario Slongo

It is certified that error appears in the above-identified patent and that said Letters Patent is hereby corrected as shown below:

Claim 1, Column 21, Line 30 should read-- alkyl, $C_5$-$C_8$ cycloalkyl, phenyl, $C_7$-$C_9$ phenylalkyl, --.

Claim 5, Column 22, Lines 42-50 should read--

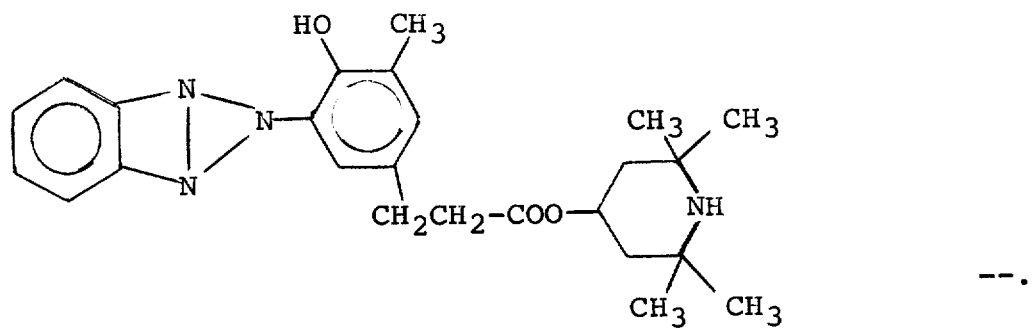

--.

UNITED STATES PATENT AND TRADEMARK OFFICE
CERTIFICATE OF CORRECTION

PATENT NO. : 4,481,315

DATED : November 6, 1984

INVENTOR(S) : Jean Rody and Mario Slongo

It is certified that error appears in the above-identified patent and that said Letters Patent is hereby corrected as shown below:

Claim 6, Column 22, Lines 56-65 should read --

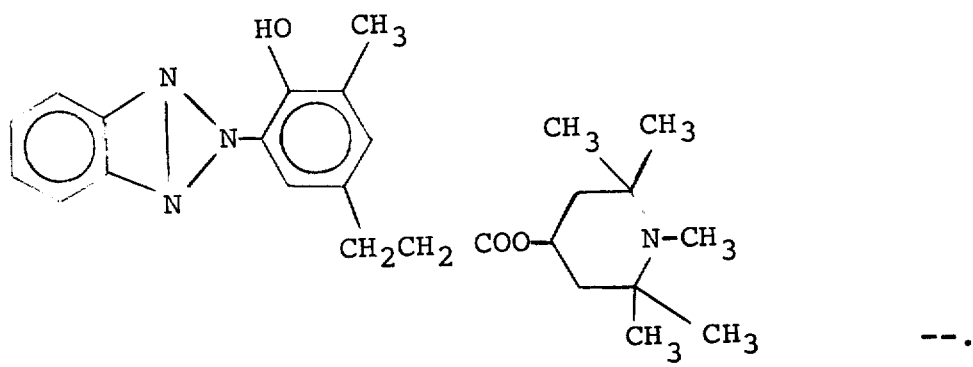

--.

Signed and Sealed this

Fifteenth Day of October 1985

[SEAL]

Attest:

DONALD J. QUIGG

Attesting Officer

Commissioner of Patents and Trademarks—Designate